United States Patent
Eggert et al.

(10) Patent No.: US 9,572,932 B2
(45) Date of Patent: Feb. 21, 2017

(54) MEDICAMENT DELIVERY DEVICE AND METHOD OF CONTROLLING THE DEVICE

(75) Inventors: Ilona Eggert, Frankfurt am Main (DE); Christopher Nigel Langley, Warwickshire (GB); Shane Alistair Day, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/119,157

(22) PCT Filed: May 24, 2012

(86) PCT No.: PCT/EP2012/059747
§ 371 (c)(1),
(2), (4) Date: Nov. 20, 2013

(87) PCT Pub. No.: WO2012/160156
PCT Pub. Date: Nov. 29, 2012

(65) Prior Publication Data
US 2014/0081234 A1    Mar. 20, 2014

(30) Foreign Application Priority Data
May 25, 2011   (EP) ..................... 11167531

(51) Int. Cl.
*A61M 5/168*    (2006.01)
*A61M 5/145*    (2006.01)
(Continued)

(52) U.S. Cl.
CPC ..... *A61M 5/16827* (2013.01); *A61M 5/14566* (2013.01); *A61M 5/19* (2013.01);
(Continued)

(58) Field of Classification Search
CPC ............ A61M 2205/50; A61M 5/16827; A61M 5/3146; A61M 5/31545; A61M 5/31546; A61M 2005/1787; A61M 2005/2407; A61M 2005/2474; A61M 2005/2496; A61M 2005/3118; A61M 2005/3128; A61M 5/14244; A61M 5/14566; A61M 5/19; A61M 5/20
See application file for complete search history.

(56) References Cited

U.S. PATENT DOCUMENTS 4,748,600 A * 5/1988 Urquhart ............... A61J 7/0418
221/15
5,464,392 A   11/1995 Epstein et al.
(Continued)

FOREIGN PATENT DOCUMENTS

EP   0985420 A2   3/2000
EP   2168616 A1   3/2010
(Continued)

OTHER PUBLICATIONS

English Translation of Second Office Action issued in Chinese Patent Application No. 201280036341.3 dated Feb. 24, 2016.

*Primary Examiner* — Quynh-Nhu H Vu
(74) *Attorney, Agent, or Firm* — McDonnell Boehnen Hulbert & Berghoff LLP

(57) ABSTRACT

Described is a needle assembly reuse prevention mechanism comprising a barrier movable between a retracted position and an extended position, a spring coupled to the barrier, a pin formed on the barrier, and a slot receiving the pin. When in the extended position, the barrier substantially covers an opening of a needle assembly storage compartment. The spring forces the barrier in a first direction. The slot has at least one abutment face for abutting the pin and preventing movement of the barrier in the first direction.

17 Claims, 12 Drawing Sheets

(51) Int. Cl.
*A61M 5/19* (2006.01)
*A61M 5/20* (2006.01)
*A61M 5/315* (2006.01)
*A61M 5/34* (2006.01)
*A61M 5/24* (2006.01)
*A61M 5/142* (2006.01)
*A61M 5/31* (2006.01)
*A61M 5/178* (2006.01)

(52) U.S. Cl.
CPC ........... *A61M 5/20* (2013.01); *A61M 5/14244* (2013.01); *A61M 5/3146* (2013.01); *A61M 5/31546* (2013.01); *A61M 5/345* (2013.01); *A61M 2005/1787* (2013.01); *A61M 2005/2407* (2013.01); *A61M 2005/2474* (2013.01); *A61M 2005/2496* (2013.01); *A61M 2005/3118* (2013.01); *A61M 2005/3128* (2013.01); *A61M 2205/50* (2013.01)

(56) References Cited

U.S. PATENT DOCUMENTS

| | | | |
|---|---|---|---|
| 5,478,323 A * | 12/1995 | Westwood et al. | 604/191 |
| 5,772,635 A * | 6/1998 | Dastur | A61M 5/172 604/131 |
| 5,782,805 A * | 7/1998 | Meinzer | A61M 5/172 604/131 |
| 6,192,891 B1 | 2/2001 | Gravel et al. | |
| 6,852,104 B2 * | 2/2005 | Blomquist | A61M 5/1452 604/504 |
| 7,041,082 B2 | 5/2006 | Blomquist et al. | |
| 7,495,546 B2 * | 2/2009 | Lintell | A61J 7/0481 128/200.14 |
| 7,753,880 B2 * | 7/2010 | Malackowski | A61B 17/1626 318/432 |
| 7,938,796 B2 * | 5/2011 | Moubayed | A61M 5/172 604/118 |
| 8,182,445 B2 * | 5/2012 | Moubayed | A61M 5/172 604/118 |
| 8,360,737 B2 * | 1/2013 | Smisson et al. | 417/44.1 |
| 2003/0060765 A1 | 3/2003 | Campbell et al. | |
| 2004/0024364 A1 | 2/2004 | Langley et al. | |
| 2004/0210199 A1 | 10/2004 | Atterbury et al. | |
| 2005/0165363 A1 | 7/2005 | Judson et al. | |
| 2005/0209563 A1 * | 9/2005 | Hopping | A61M 1/28 604/151 |
| 2007/0088269 A1 * | 4/2007 | Valego | A61M 5/142 604/151 |
| 2007/0088271 A1 * | 4/2007 | Richards | A61M 5/14244 604/151 |
| 2007/0161970 A1 | 7/2007 | Spohn et al. | |
| 2008/0146996 A1 * | 6/2008 | Smisson | A61M 1/0281 604/67 |
| 2011/0313349 A1 | 12/2011 | Krulevitch et al. | |

FOREIGN PATENT DOCUMENTS

| | | |
|---|---|---|
| WO | WO 93/12825 A1 | 7/1993 |
| WO | WO 00/28217 A1 | 5/2000 |
| WO | WO 2010019456 A1 | 2/2010 |
| WO | 2010098929 A1 | 9/2010 |
| WO | 2011039219 A2 | 4/2011 |

* cited by examiner

MEDICAMENT DELIVERY DEVICE AND METHOD OF CONTROLLING THE DEVICE

CROSS REFERENCE TO RELATED APPLICATIONS

The present application is a U.S. National Phase Application pursuant to 35 U.S.C. §371 of International Application No. PCT/EP2012/059747 filed May 24, 2012, which claims priority to European Patent Application No. 11167531.0 filed May 25, 2011. The entire disclosure contents of these applications are herewith incorporated by reference into the present application.

FIELD OF INVENTION

This invention relates to a medicament delivery device, and method of controlling the device, for the administration of one or more drug agents to a patient, and in particular but not exclusively, for the self-administration of the drug agent(s).

BACKGROUND

Certain disease states require treatment using one or more different medicaments. Some drug compounds need to be delivered in a specific relationship with each other in order to deliver the optimum therapeutic dose. Although the present patent application is applicable to single medicament devices, it is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of one or more medicament in a single injection or delivery step that is simple for the user to perform without complicated physical manipulations of the drug delivery device. In the case of a combination therapy device, the proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the reservoir in the case of a single medicament device or, in the case of a combination therapy device, a primary reservoir and with a secondary reservoir of medicament containing at least one drug agent. The drug dispense interface can be a type of outlet that allows the two or more medicaments to exit the system and be delivered to the patient.

In cases where the device is applicable to a combination therapy, the combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

In practical use of medical devices of the above mentioned type, whether they be for single or plural medicament delivery, it may be desirable to ensure priming of the device in some circumstances.

A known medicament delivery device has a priming function for discharging air from the device or reservoir prior to administration of the medicament to the patient. This prime function has been achieved by holding the needle upward and operating the drive mechanism until a quantity of medicament is seen at the needle tip by the user. On seeing a drop of medicament at the needle tip, the user can be assured that medicament rather than air is injected into the body of the patient. However, such devices place a burden on the user to remember when to exercise a priming operation. An undesirable consequence of failing to prime the device is that there may be an under dose of medicament owing to the injection of air into the patient. A further difficulty is a risk of excessive or unnecessary priming of medicament, leading to reduction in the number of doses remaining in the reservoir. This difficulty is particularly apparent in combination therapy devices that contain two medicaments, one being in relatively low volume relative to the other.

The invention therefore faces the technical problem of reducing a risk of unnecessary priming in an above mentioned medical device and at the same time increasing user operability as between delivery of the priming and dose delivery modes.

It is an aim of the present invention to alleviate the aforementioned difficulties. It is a further aim to simplify user priming of the medicament delivery device. It is also an aim of the present invention to alleviate the problem of medicament loss through priming actions.

According to a first aspect of the present invention, there is provided a medicament delivery device for the administration of one or more drug agents to a patient, the device having a priming mode and a drug delivery mode for administering delivery of the one or more drug agents to the patent, wherein the device comprises a controller operative for: setting the device in a priming mode when one or more predetermined states of the device are identified and for disabling the drug delivery mode during said one or more predetermined states; and, when states of the device are different from said one or more predetermined states, setting the device in the drug delivery mode while maintaining enablement of the priming mode through a user interface. In a preferred embodiment, the user can select between the priming mode and the drug delivery mode through the user interface.

A device embodying the first aspect of the present invention may provide for a simpler user interface by setting a mandatory priming mode when warranted by the status of the device, while providing a user option of selecting an additional or optional prime function prior to other operational states of the device, such as setting and injecting a dose. The device may thereby reduce medicament loss due to excessive or unnecessary priming.

According to a second aspect of the present invention, there is provided a medicament delivery device for the administration of one or more drug agents to a patient, the device having a priming mode and a drug delivery mode for administering delivery of the one or more drug agents to the patent, wherein the device comprises a controller operative for setting the device in a priming mode and for selecting a preset quantity or source of medicament to be ejected from the device, the preset quantity or source varying in dependence on which one of a plurality of operational states of the device are identified by the controller.

In a preferred embodiment of the second aspect, at least one of said plurality of operational states may be identified as any one of: a successive dose state when a predetermined period of time has elapsed since a previous dose delivered to the patient; or a previous priming state when a predetermined period of time has elapsed since a previous priming of the device. The device may include a detachable dispense interface for providing fluid communication from the device to an outlet, wherein one of said plurality of operational states is identified as a dispense interface prime state when the dispense interface is placed on the device. In this case, the device may comprise a first retainer and a second retainer each for holding a medicament reservoir or cartridge containing a drug agent, the controller being operative to deliver the drug agents to the patient. In one embodiment of the second aspect, the controller may be operative to select the preset quantity or source of medicament from both of the first and second retainers when any one or more of: a) the dispense interface prime state is identified; b) the successive dose is identified and the predetermined period of time exceeds a preset value; or c) the previous priming state is identified and the predetermined period of time exceeds a preset value. Alternatively or in addition the controller may be operative to select the preset quantity or source of medicament from a designated one of the medicament reservoirs or cartridges of the first and second retainers when either the: a) successive dose state is identified and the predetermined period of time is less than a preset value; or b) a previous priming state is identified and the predetermined period of time is less than a preset value.

The first and second aspects are applicable to single therapy devices which have a single medicament stored in a single reservoir or cartridge. However, in the case of a combination therapy device, the one or more drug agents may comprise first and second medicaments stored in first and second reservoirs. The medicaments may be the same as or different from one another. The device may have a dose setting mechanism for user setting of an appropriate dose of the one or more drug agents, and a drive mechanism for automatic or manual delivery of the drug agent(s) to the patient. The device may comprise a prompt to prompt the user to prime the device when said predetermined state has been identified. A priming operation may be desired by a user or patient for confidence that air and/or residual medicament from a previous dose is cleared prior to injection of medicament into the patient. It may be performed by advancing the drive mechanism a small distance to cause one or a few drops of medicament to appear at the needle tip of the device. If the user does not see a drop of medicament another priming operation may be selected.

Devices embodying the first or second aspects of the present invention may include a detachable dispense interface for providing fluid communication from the device to an outlet. The outlet may include an attachment for a needle hub. The device may be capable of sensing attachment or detachment therefrom of a needle hub and/or the dispense interface, so that one of the predetermined states includes identification of a dispense interface prime state when the dispense interface or the needle hub is placed on the device. In devices embodying the first or second aspects of the present invention, one of said predetermined states may be identified as a dispense interface prime state when the dispense interface is identified as being attached to the device and no dose of medicament has been dispensed from the device since the attachment of the dispense interface to the device. In these cases, the controller is operative to mandate a priming function in order to ensure or give confidence to the user that air is expelled from the needle hub and/or the dispense interface in preparation for use of the device to inject a dose of medicament or medicaments into the patient.

As the controller is able to discriminate between different states, the device may be programmed using appropriate software routines to respond in a manner that is appropriate for any given operational state of the device, thereby reducing a risk of ambiguous options being available to the user. For example, as indicated above there may be circumstances where a priming function is deemed mandatory and other situations where the priming function may be provided as an option to the user prior to setting a dose. When the device provides the user with an option to prime or dose, the user may perform a plurality of priming operations in order to ensure a drop or drops of medicament appear at the needle tip, thereby assuring the user that the device is ready for injection.

Devices that can accommodate more than one drug agent reservoir or cartridge may include a first retainer and a second retainer for holding a medicament reservoirs or cartridges containing two drug agents that may be the same as or different from one another. The medicament reservoirs or cartridges may contain independent (single drug compound) or pre-mixed (co-formulated multiple drug compounds). The dispense interface for a device having first and second retainers may be provided with a bifurcated conduit for providing fluid communication from the first and second retainers to a unitary outlet. The needle hub may be removably attached to the unitary outlet. The priming function is achieved by control of a drive mechanism by the controller to eject a quantity of medicament from the device. The quantity of medicament is preset by the controller. This priming function is effective for devices having one medicament reservoir or cartridge or more than one medicament reservoir or cartridge. In the latter case, the drive mechanism is operative to eject a quantity of medicament from each cartridge to expel air or medicament from a previous dose from the device. The controller is operative to eject the drug agents to the patient simultaneously and/or successively when the device is in the priming mode as well as when the device is in the drug delivery mode.

The control unit preferably comprises a control panel with input means, such as buttons or the like, as well as output means, such as a digital display or a sound unit or the like. The input means may be configured to receive inputs from a user, whereas the output means may be configured to indicate information, permissible/disallowed functions, prompts or guidance to the user.

Once the mandatory priming function has been executed, the device is set in a drug delivery mode while maintaining enablement of the priming mode, whereby the user can select between the priming mode to perform an additional prime or to proceed to the drug delivery mode. In this mode, and in the event the user opts for an additional prime by selecting the appropriate indication via the display and toggle or button, the controller primes the device from a designated one of the medicament reservoirs or cartridges of the first and the second retainers, provided the time that has elapsed between successive doses or since a previous priming of the device is less than a predetermined value set between, for example, 1 and 24 hours. This operational function is to preserve medicament from the non-designated one of the medicament reservoir or cartridge that might otherwise be dispensed by a user-optional prime. If when the user opts for an additional prime when the time that has elapsed between successive doses or since a previous priming of the device is greater than a predetermined value set between, for example 1 and 24 hours, then the controller is operative for priming the device from both of the medicament reservoirs or cartridges of the first and the second retainers. This is so that the device refreshes the medicament in the needle hub or dispense interface before setting the dose delivery mode.

A device embodying the second aspect of the present invention has the benefit of providing an improved control of the priming function whereby loss or wastage of medicament due to unnecessary or excessive priming can be reduced. In a device having more than one medicament, the controller may be configured to control the quantity or source of one medicament dispensed during a priming function to be less than the quantity or volume of another medicament. In this way, the quantity dispensed due to priming of a more expensive medicament or one contained in a smaller reservoir or cartridge can be reduced or minimised. In other words, the controller may preferentially dispense a less expensive or lower volume medicament during the priming mode. The controller may be optionally programmed to dispense medicament from only one of the reservoirs or cartridges when the device is primed at the option of the user.

The controller may include an electronic control unit that may comprise at least an evaluation unit, which is configured to receive signals from a sensor unit. In this configuration the sensor unit may be an electronic or an electromechanical sensor, which is configured to send signals to the evaluation unit dependant on the positions of the medicament or cartridge retainers and/or locking conditions of locking devices provided to retain the medicament reservoirs or cartridges in the device. There may also be a sensor unit, which is configured to send signals to the evaluation unit dependant on the correct insertion of the medicament reservoirs. There may further be a sensor unit, which is configured to send signals to the evaluation unit dependant on the filling level of the medicament reservoirs. The sensor units and the evaluation unit may also be one component.

The digital display may be configured to show if a cartridge retainer is open and which medicament reservoir, filled with what type of medicament, has to be inserted into the opened cartridge retainer. Likewise the digital display and the sound unit may be configured to indicate if a medicament reservoir has not properly been inserted into the respective cartridge retainer. The output means may further be configured to indicate information concerning the filling level of the medicament reservoirs.

According to another aspect of the present invention, there is provided a method of controlling a medicament delivery device for the administration of one or more drug agents, the method comprising: identifying when the device is in a predetermined state; setting the device in a priming mode when said predetermined state of the device is identified; disabling a drug delivery mode of the device when said predetermined state is identified; identifying when the device is in a state that is different from said predetermined state; setting the device in the drug delivery mode while maintaining enablement of the priming mode when the state different from said predetermined state is identified; and facilitating selection between the priming mode and the drug delivery mode when the device is in said different state.

According to yet another aspect of the present invention, there is further provided a method of controlling a medicament delivery device for the administration of one or more drug agents, the method comprising: identifying an operational state of the device from a plurality of predetermined operational states; selecting a preset quantity of medicament to be ejected from the device; and varying the preset quantity in dependence on which one of the plurality of operational states of the device are identified by the controller. In a device having more than one medicament cartridge, varying the quantity may include varying the source to preferentially dispense the priming dose from a predetermined cartridge.

According to a yet further aspect of the present invention, there is provided a computer program, comprising code which when run on a processor is operative to control a medicament delivery device for the administration of one or more drug agents, and to control the device to:

identify when the device is in a predetermined state;
set the device in a priming mode when said predetermined state of the device is identified;
disable a drug delivery mode of the device when said predetermined state is identified;
identify when the device is in a state that is different from said predetermined state;
set the device in the drug delivery mode while maintaining enablement of the priming mode when the state different from said predetermined state is identified; and
facilitate selection between the priming mode and the drug delivery mode when the device is in said different state.

According to a still further aspect of the present invention, there is provided a computer-readable medium encoded with instructions that, when executed on a computer, control a medicament delivery device for the administration of one or more drug agents by:
identifying when the device is in a predetermined state;
setting the device in a priming mode when said predetermined state of the device is identified;
disabling a drug delivery mode of the device when said predetermined state is identified;
identifying when the device is in a state that is different from said predetermined state;
setting the device in the drug delivery mode while maintaining enablement of the priming mode when the state different from said predetermined state is identified; and
facilitating selection between the priming mode and the drug delivery mode when the device is in said different state.

The medicament delivery device may be an infusion device or an injection device, for example, a hand-held insulin injection pen. The medicament delivery devices embodying the present invention may be used either by medical personnel or by patients themselves. As an example, type-1 and type-2 diabetes may be treated by patients themselves by injection of insulin doses, for example once or several times per day. The first and second retainers may be configured to hold medicament reservoirs or cartridges that contain different drug agents from one another, for example, a fast acting insulin drug agent in one and a long acting insulin drug agent in the other. The first and second retainers are preferably sized differently from one another to ensure the user places the correct drug agent in the correct retainer. In embodiments of the present invention, the controller may be programmed by software to perform the operations of the device and to indentify the predetermined states and non-predetermined states of the device.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
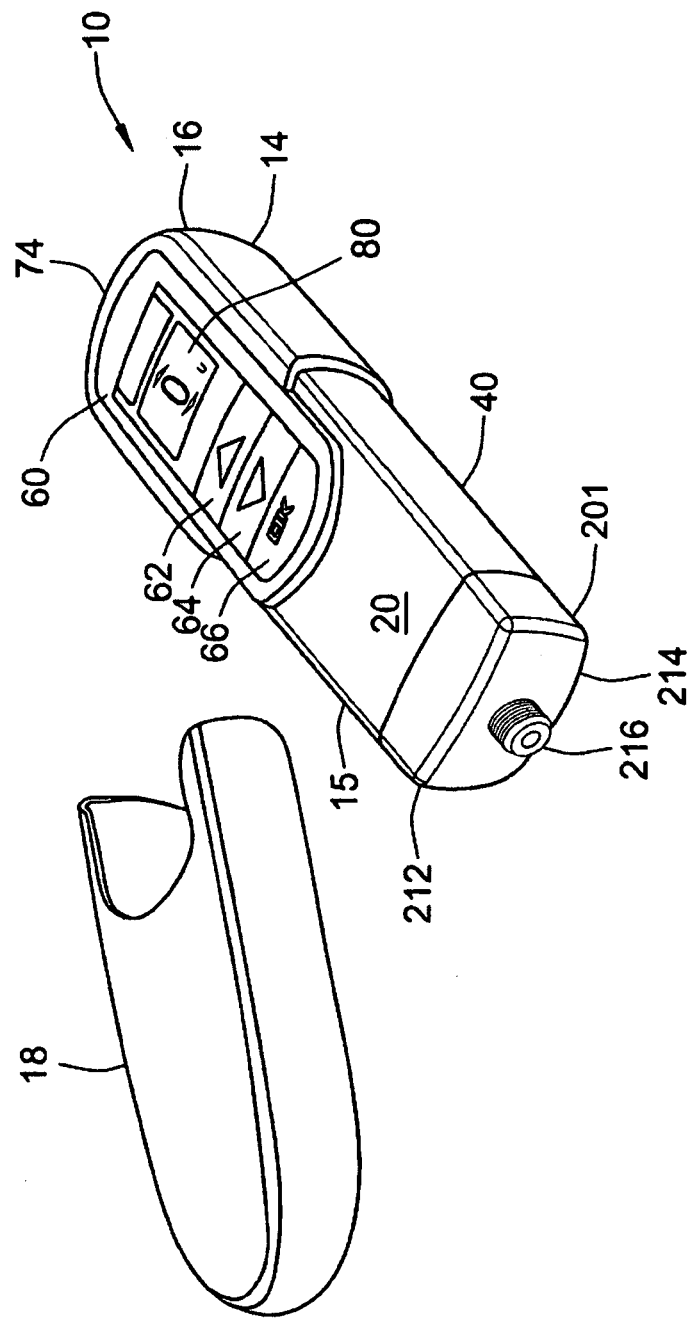
FIG. 1 illustrates a perspective view of a single medicament cartridge delivery device embodying the present invention with an end cap of the device removed.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and a single retainer for holding a medicament reservoir or cartridge. When the end cap or cover 18 is removed from the device 10 (as illustrated in FIG. 1), a dispense interface 201 is mounted to the distal end 15 of the main body 14, and a dose dispenser (e.g., a needle assembly) is attached to the interface. The dispense interface 201 provides a fluidic communication between the needle assembly and the medicament reservoir held within the device. The drug delivery device 10 can be used to administer a computed dose of a medicament through a single needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK". In addition, along the most proximal end of the main body, an injection button 74 is also provided (not visible in the perspective view of FIG. 1). A cartridge holder 40 can be removably attached to the main body 14 and may contain a single cartridge retainer (not shown).

Figure 2:
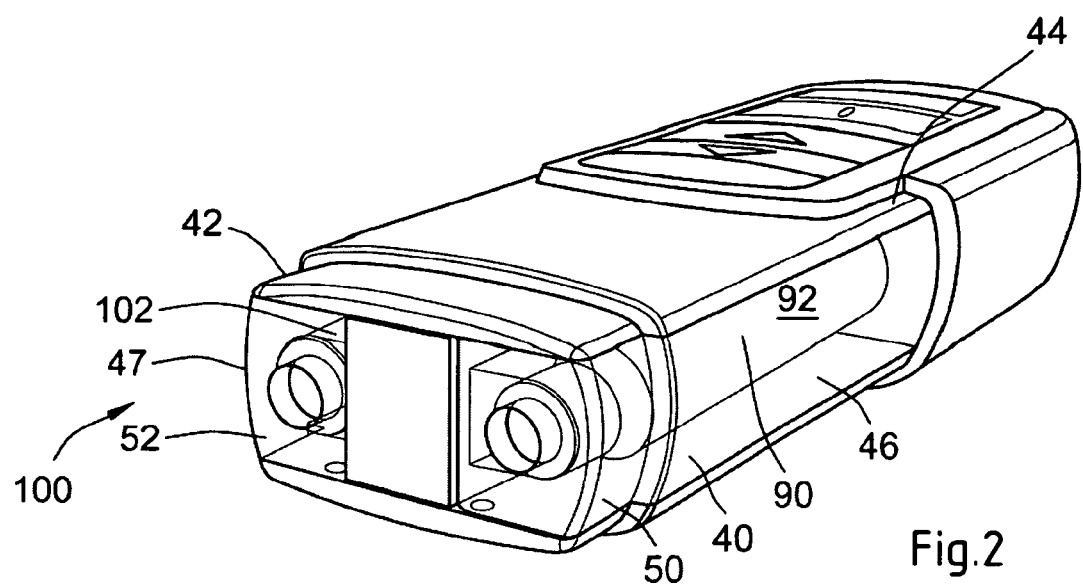
FIG. 2 illustrates a perspective view of the delivery device of FIG. 1 except that it has dual medicament cartridges.

The embodiment shown in FIG. 2, has similar elements to the embodiment of FIG. 1 except that the cartridge holder 40, which can also be removably attached to the main body 14, may contain at least two cartridge retainers 50 and 52.

Each retainer is configured so as to contain one medicament reservoir, such as a glass cartridge. Preferably, each cartridge contains a different medicament.

In addition, at the distal end of the cartridge holder 40, the drug delivery device illustrated in FIG. 2 includes the dispense interface 200 for providing fluidic communication between the needle assembly and the medicament reservoirs held within the device. As will be described in relation to FIG. 4, in one arrangement, this dispense interface 200 includes a main outer body 212 that is removably attached to a distal end 42 of the cartridge holder 40. As for the embodiment of FIG. 1, a distal end 214 of the dispense interface 201 is similarly provided and preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 of the FIG. 1 and FIG. 2 embodiments illuminates and provides the user certain device information, preferably information relating to the medicament(s) contained within the cartridge holder 40. For example, the user is provided with certain information relating to the single medicament of FIG. 1 or both the primary medicament (Drug A) and the secondary medicament (Drug B) of FIG. 2.

Figure 3:
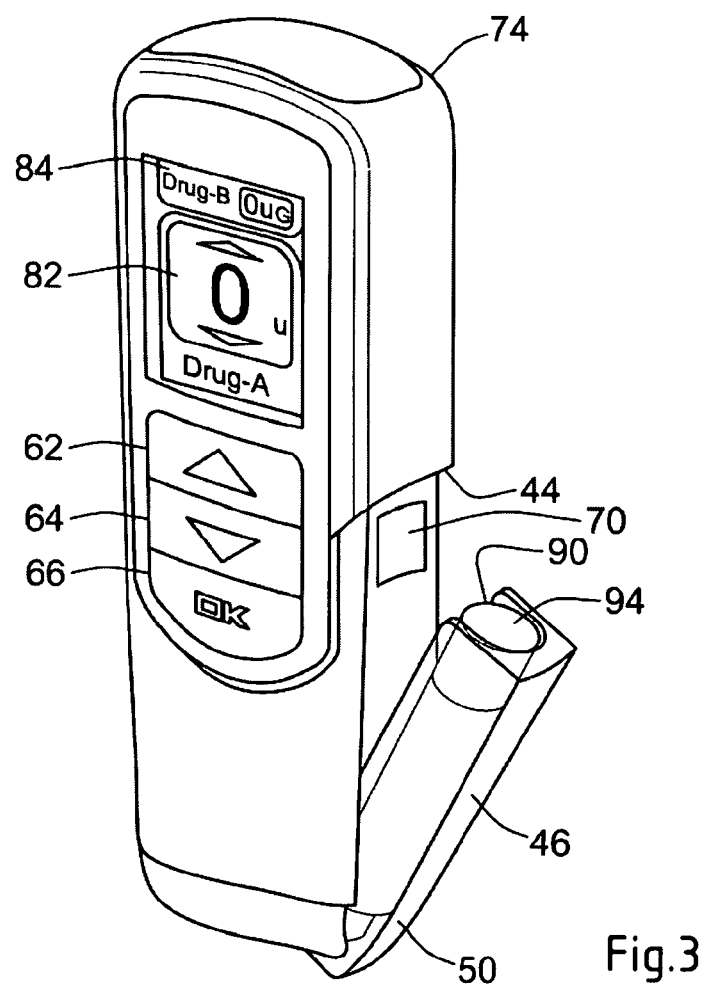
FIG. 3 illustrates a perspective view of the cartridge retainer illustrated in FIG. 2 with one cartridge retainer in an open position.

As shown in FIG. 3, first and second cartridge retainers 50, 52 comprise hinged cartridge retainers. These hinged retainers allow user access to the cartridges. FIG. 3 illustrates a perspective view of the cartridge holder 40 with the first hinged cartridge retainer 50 in an open position. FIG. 3 illustrates how a user might access the first cartridge 90 by opening up the first retainer 50 and thereby having access to the first cartridge 90. The cartridge holder 40 of FIG. 1 is provided with a single retainer similar to either retainer 50 or 52 of the embodiment of FIG. 2.

Figure 4:
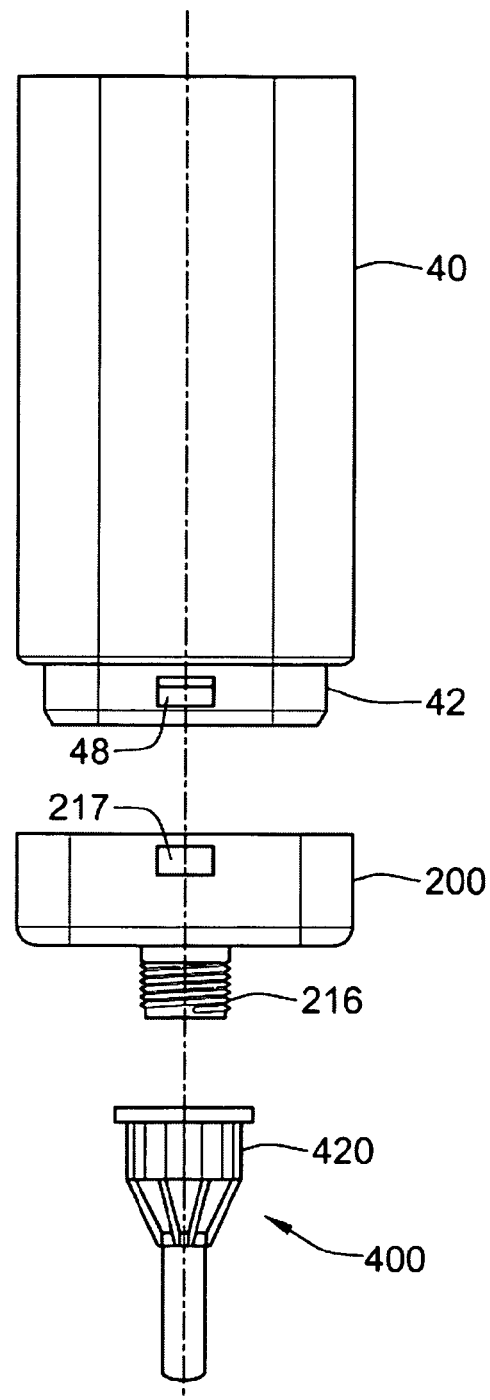
FIG. 4 illustrates a dispense interface and a dose dispenser that may be removably mounted on a distal end of the delivery device illustrated in FIG. 2.

The dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
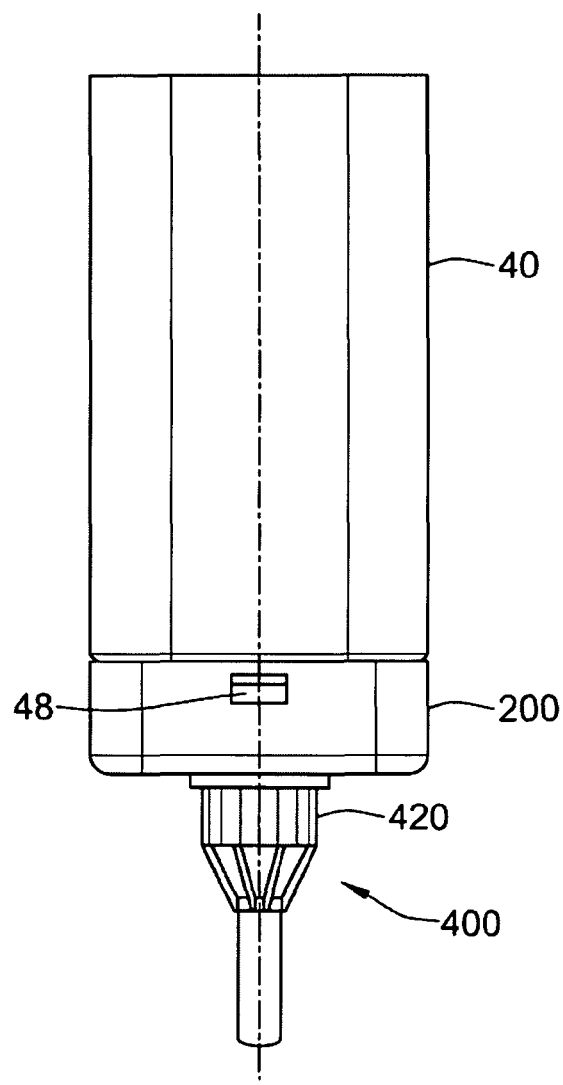
FIG. 5 illustrates the dispense interface and the dose dispenser illustrated in FIG. 4 mounted on a distal end of the delivery device illustrated in FIG. 2.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
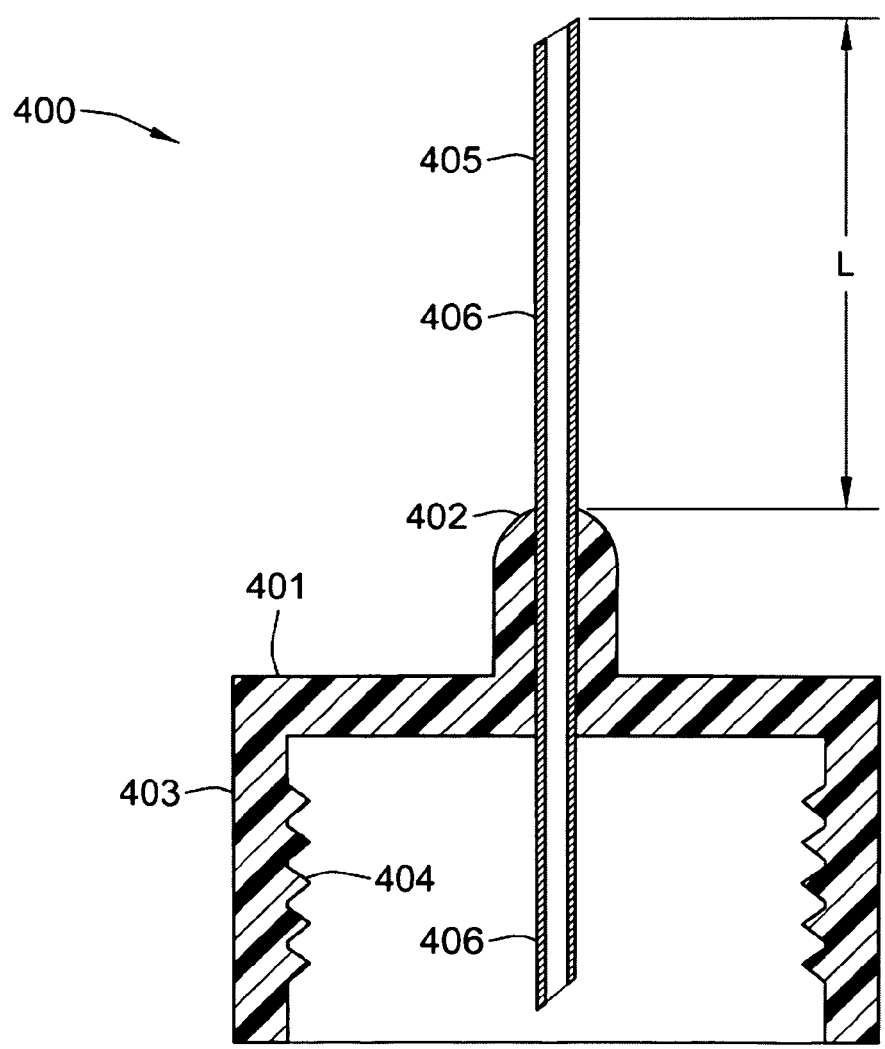
FIG. 6 illustrates one arrangement of the dose dispenser that may be mounted on a distal end of the delivery device of either FIG. 1 or FIGS. 2-5.
Figure 7:
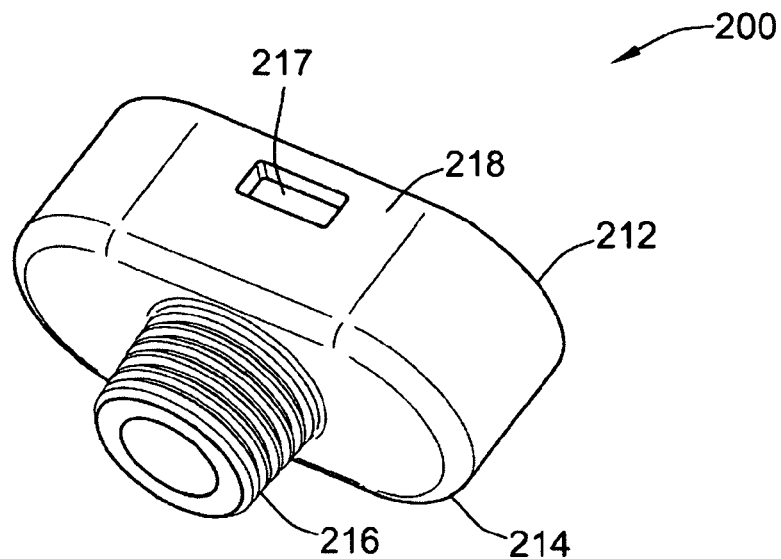
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of a dispense interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge holder 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

Figure 8:
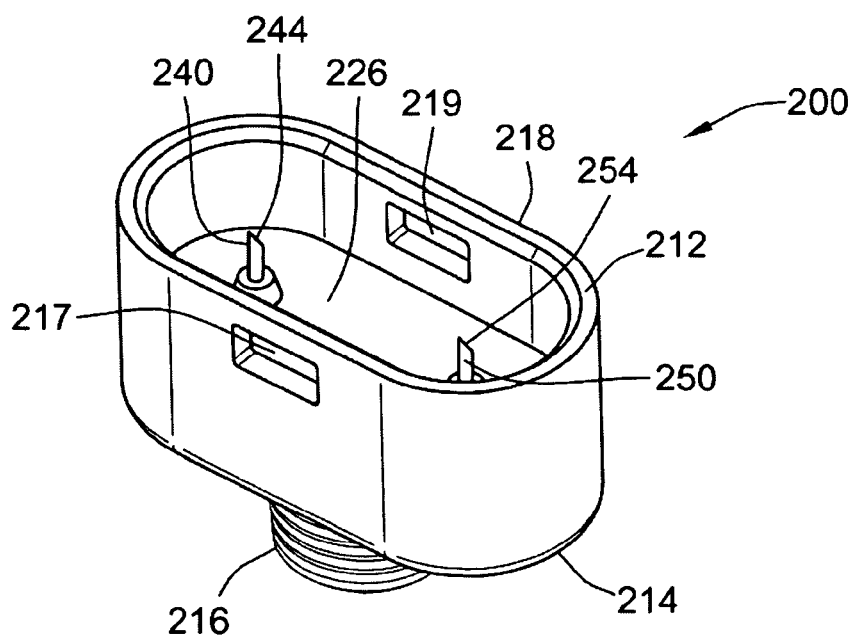
FIG. 8 illustrates another perspective view of the dispense interface illustrated in FIG. 4.
Figure 9:
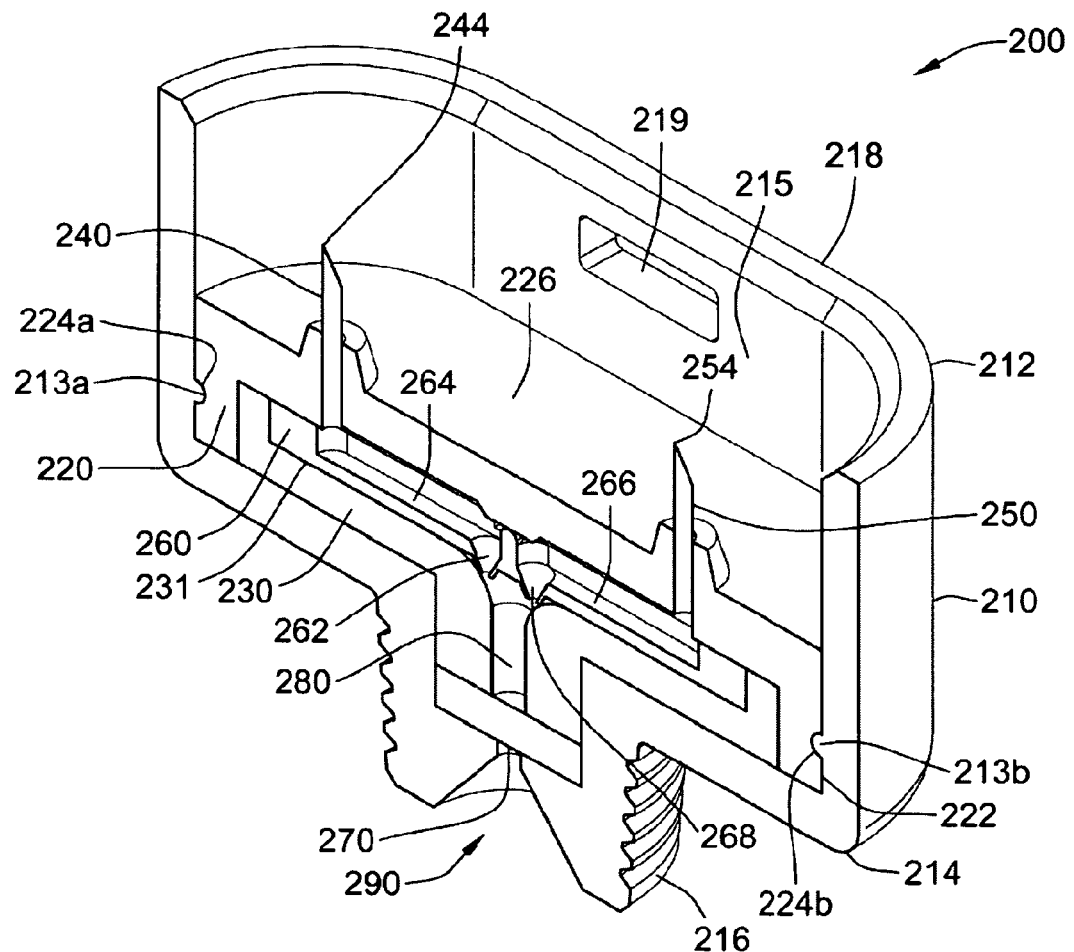
FIG. 9 illustrates a cross-sectional view of the dispense interface illustrated in FIG. 4.
Figure 10:
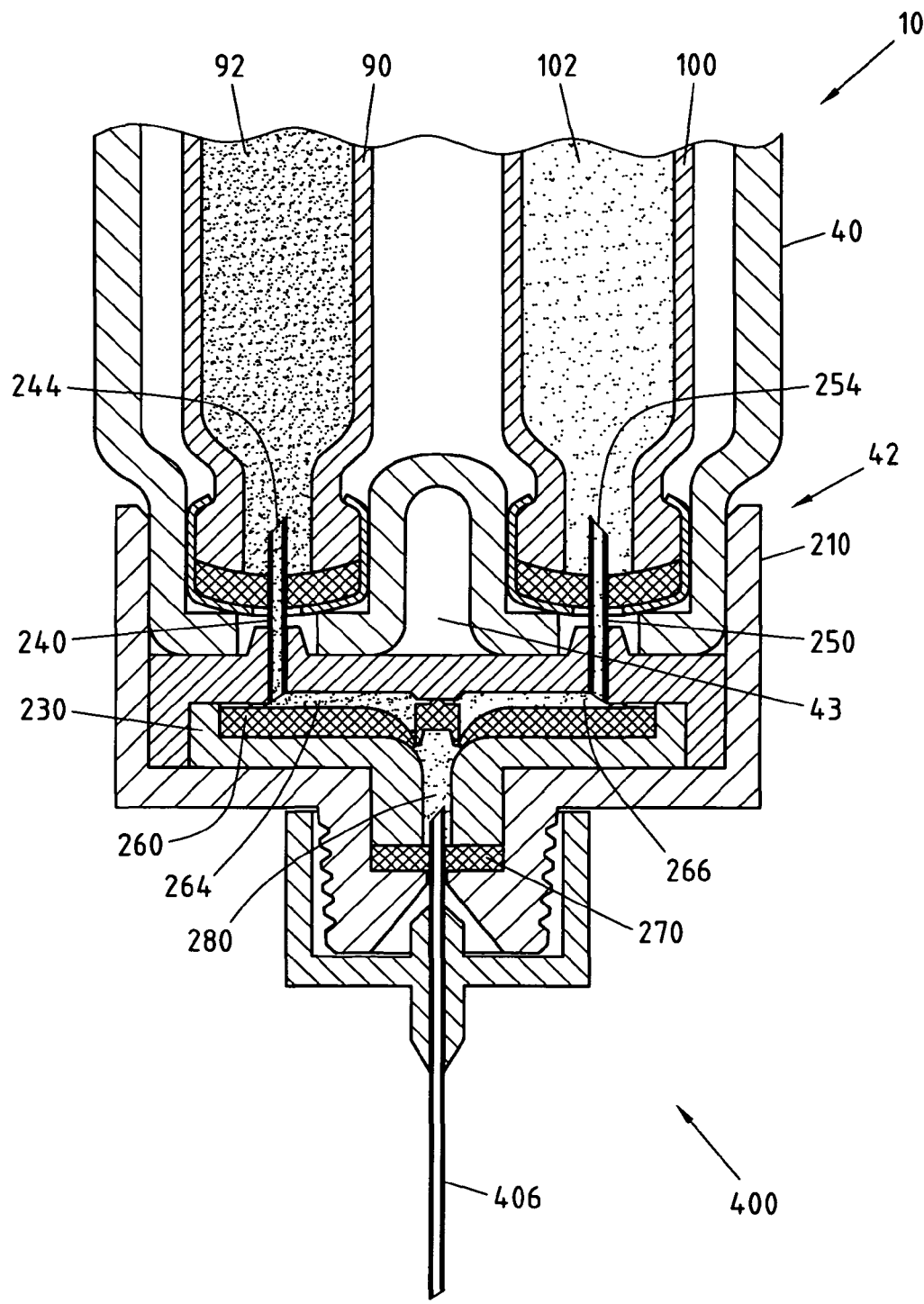
FIG. 10 illustrates a cross-sectional view of the dispense interface and dose dispenser mounted onto a drug delivery device, such as the device illustrated in FIG. 2.

The dispense interface 200 further comprises a first inner body 220. Certain details of this inner body are illustrated in FIG. 8-10. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

FIG. 10 illustrates the dispense interface 200 after it has been mounted onto the distal end 42 of the cartridge holder 40 of the drug delivery device 10 illustrated in FIG. 2. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 10 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 10, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 10, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

It will be apparent that when the medical device 10 is brought into use, there may be a need or desire to execute a priming operation. For example, if the dispense interface has been changed there will be air in the first and second fluid conduits 264, 266 and the holding chamber 280 of the dispense interface 200 as well as the cannula 406 of the needle hub 400. Consequently, it is desirable to prime the device 10 by ejecting medicament through the conduits until medicament appears at the distal end of the needle hub 400; thereby ensuring that air has been expelled from the fluid communication channels between the cartridges 90, 100 and the end of the cannula 406 to be inserted into a patient. Furthermore, in the event of replacement of one or both of the cartridges 90, 100, it may be a functional requirement programmed into the device that the dispense interface 400 be removed before either one of the retainers 50, 52 can be unlocked. In this case, the device 10 will require priming after replacement of the cartridge and replacement of the dispense interface 200 or a new dispense interface 200. The volume of the conduits within the dispense interface 200 to be filled during priming may be in the order of 1 μl. The priming of the device 10 will be described in more detail with reference to FIG. 13 below.

Figure 11A:
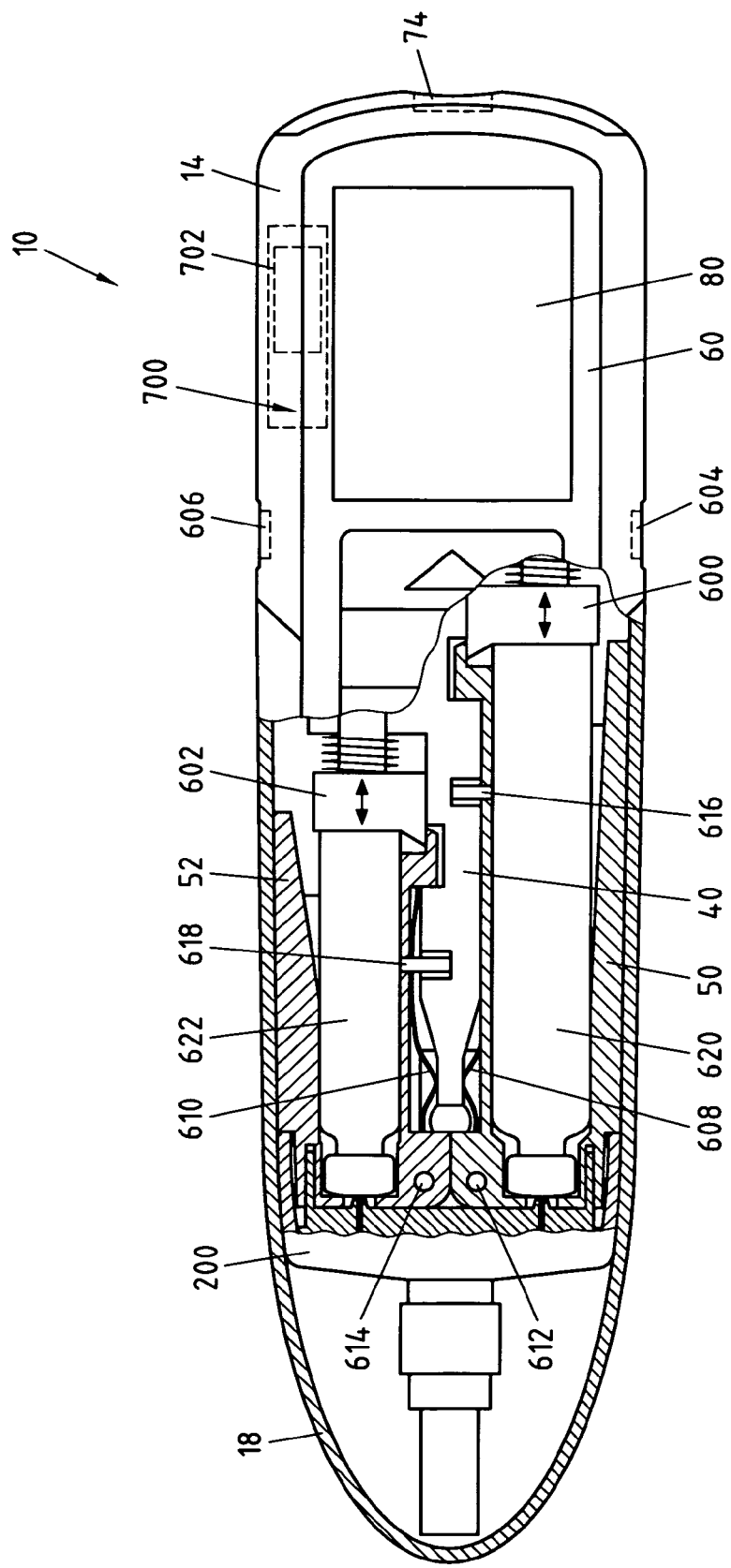
FIG. 11a illustrates a part cross-sectional view of the medical device, showing cartridges and a display.

FIG. 11a illustrates the medical device 10 in cross sectional view. The two cartridge retainers 50 and 52 are illustrated in the closed position. Retainer 50 is configured so as to contain medicament reservoir 620, whereas retainer 52 is configured so as to contain medicament reservoir 622. The reservoirs 620, 622 may be glass, metal or plastic cartridges. Reservoir 622 may have a smaller diameter and a shorter length than reservoir 620.

The cartridge holder 40 may further comprise two locking devices 600 and 602. The locking devices 600 and 602 may be designed as latches, which may lock the cartridge retainers 50, 52 in a form-fitting manner in their closed position.

The locking devices 600 and 602 may be released or unlocked by operation of the cartridge release buttons 604 and 606. The cartridge release buttons 604 and 606 may work mechanically or electromechanically.

The cartridge holder 40 further contains two cartridge retainer springs 608 and 610, which in the closed position of the cartridge retainers 50 and 52 exert an elastic spring force on the cartridge retainers. By releasing the locking devices 600 and 602 the spring force causes the cartridge retainers 50 and 52 to move in the open position.

Cartridge retainer 50 is hinged to the cartridge retainer housing at pivot bearing 612, whereas cartridge retainer 52 is hinged to the cartridge retainer housing at pivot bearing 614. The cartridge retainers 50, 52 are thereby pivotable about the pivot bearings 612, 614 between their closed and their open position.

The cartridge holder 40 may also comprise cartridge detect switches 616 and 618. The cartridge detect switches 616 and 618 may be configured to detect the insertion condition of the respective medicament cartridges 620, 622 and/or the closing condition of the cartridge retainers 50 and 52.

The apparatus 10 further comprises a controller 700, which may be a micro-processor control unit having programmed therein software for performing the functions of the device, as will be described in more detail with reference to FIGS. 12 and 13 below. The controller 700 may comprise an evaluation unit 702, which may be configured to receive signals from the cartridge detect switches 616 and 618. The evaluation unit 702 may also be configured to receive signals from sensors that are configured to determine the filling level of the cartridges 620, 622.

The controller 700 preferably is connected to a user interface, for example the control panel region 60. Preferably, the user interface or control panel region 60 comprises output means such as the digital display 80 and input means such as a keyboard, for example comprising dose setting buttons 62 and 64 or the button 66 designated with the symbol "OK" (shown in a different position in the embodiment of FIGS. 1-3 from the embodiment of FIG. 12). At the proximal end of the main body 14, further an injection button 74 is provided.

Figure 11B:
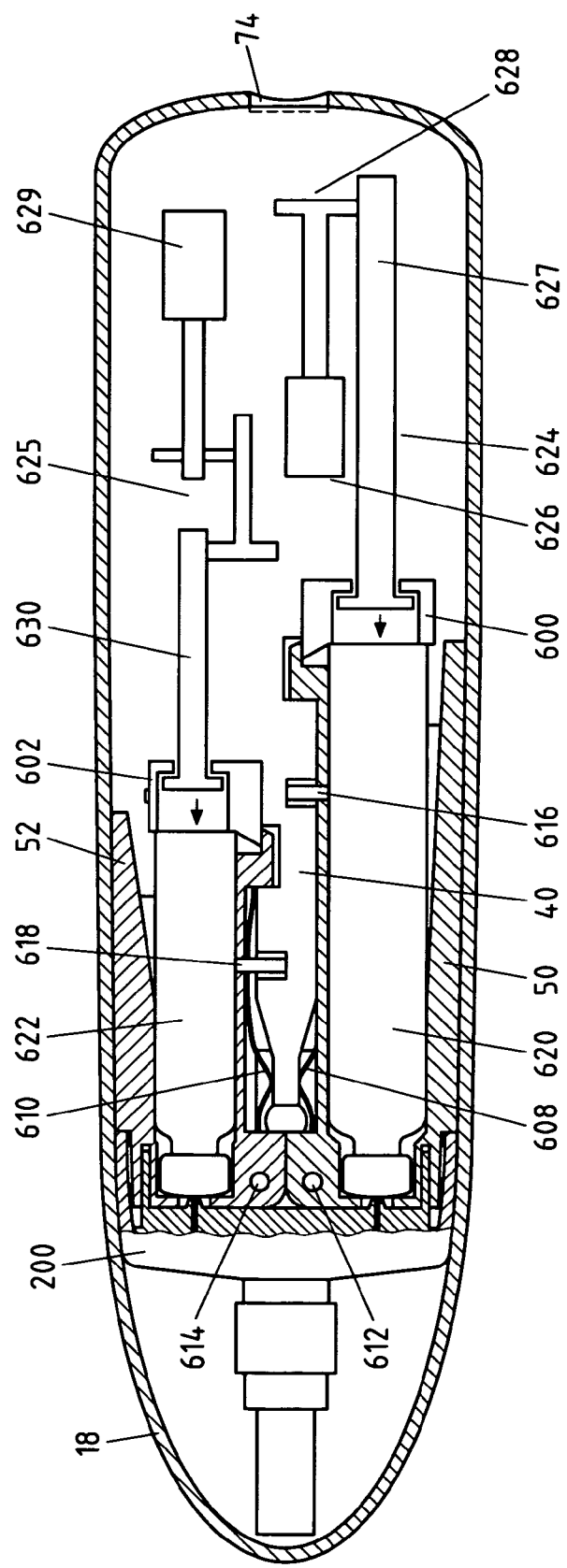
FIG. 11b illustrates a cross-sectional view of the medical device showing cartridges and a drive mechanism.

FIG. 11b is a similar view to FIG. 11a except in full cross-section showing a schematic view of a pair of drive trains 624 and 625. The first drive train 624 of the pair includes a motor 626 that drives a piston rod 627 via a gear 628. The drive train 624 is operative to drive the piston rod 627 under the control of the controller 700 to dispense medicament from the cartridge 620. A second drive train 625 includes a motor 629 for driving a piston rod 630 via a second gear mechanism 631, to dispense medicament from the cartridge 622 also under the control of the controller 700.

Figure 12:
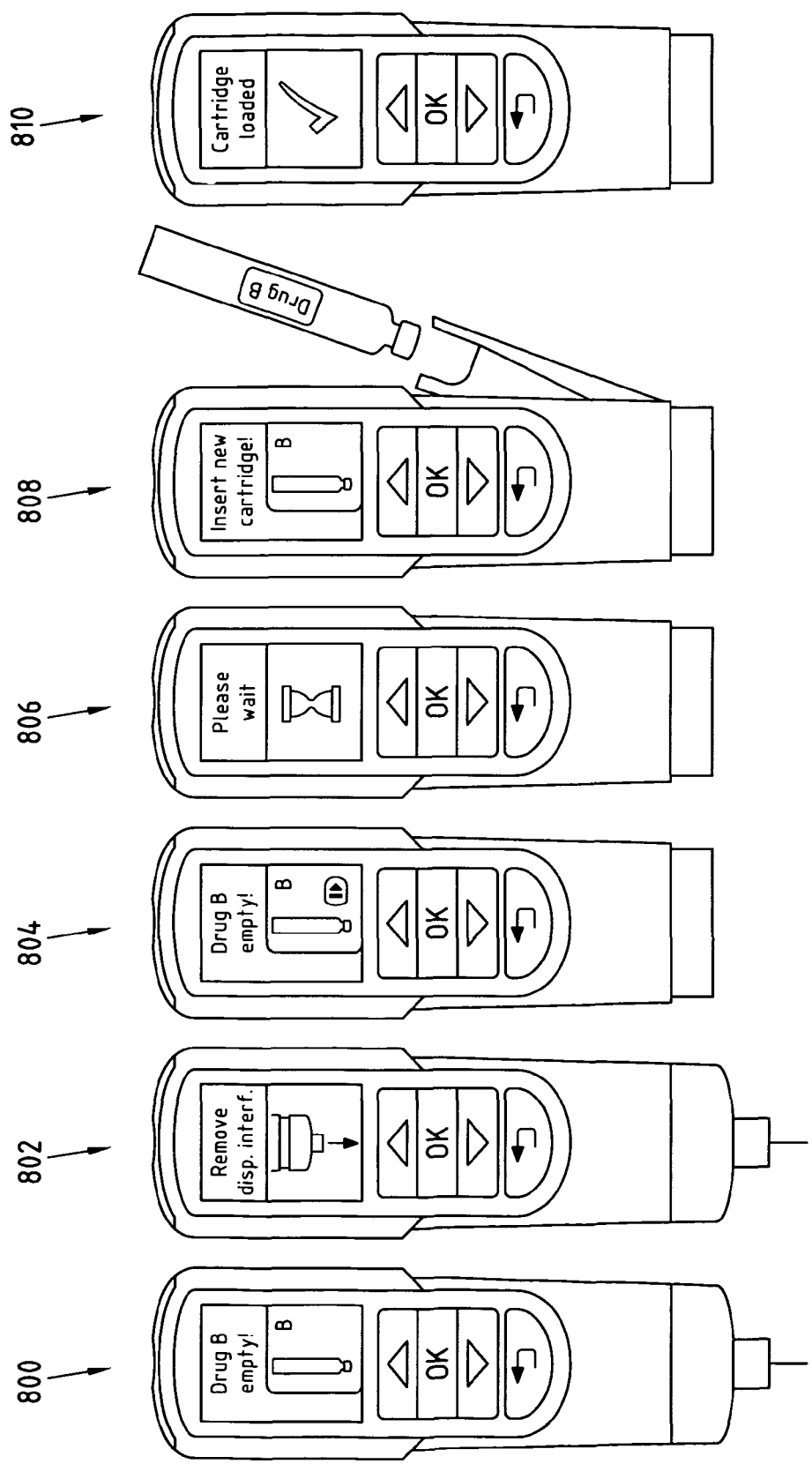
FIG. 12 illustrates a process for exchanging a medicament reservoir in the medical delivery device.

FIG. 12 illustrates the process of exchanging a cartridge in a medical delivery device 10. In step 800 the controller 700 of the medical device 10 determines that the cartridge in retainer 50 is empty and so the controller 700 goes into a 'cartridge exchange or replacement mode'. Accordingly, the digital display 80 indicates that drug B is empty. Likewise in step 800 the digital display 80 illustrates the cartridge 620 which has a big diameter and a great length as being the one that needs exchanging.

Before the user is allowed access to the cartridge holder 50, the device instructs the user to remove the dispense interface at step 802. This is indicated on the digital display 80. The indications on the digital display 80 shown in steps 800 and 802 may alternate during a certain period. Subsequently, the dispense interface 200 is removed from the cartridge holder 40 in step 802.

In step 804 the controller 700 determines the dispense interface 200 being removed from the cartridge holder 40. Further in step 804 the controller 700 may operate the locking devices 600 and 602 into an unlockable condition, in case they have been in a not-unlockable condition while the dispense interface 200 has been attached to the cartridge holder 40. At the same time the digital display 80 indicates to operate the cartridge release button 604 corresponding to the cartridge to be exchanged. When the user presses the cartridge release button 604, the controller 700 causes the drive mechanism 624 to retract the piston rod 627 from the cartridge 620, displaying a "Please wait" instruction on the display at step 806 as the piston rod 627 is retracted from the cartridge 620. When the piston rod 627 is fully retracted, the motor 626 stalls and a signal is sent to the controller 700 to trigger the locking device 600 into an unlocked or released condition thus allowing the cartridge release button 604 to open the cartridge retainer 50. At the time of the motor stall, an encoder (not shown) for monitoring the drive mechanism is put into a "datum reset" condition by the controller 700. Also, at this time, the locking device 602 is operated into a non-unlockable condition, in case this has not been conducted before so that only one cartridge retainer 50, 52 can be opened at a time.

In step 808 the cartridge retainer 50 is pushed out of the closed position into the open position by the cartridge retainer spring 608. It is also possible that cartridge retainer 50 is pulled out into the open position by the user, without the aid of elastic spring forces. As soon as the cartridge retainer 50 has been opened, the detection switch 616 sends an according signal to the controller 700. The digital display 80 subsequently indicates to insert a new cartridge 622, filled with drug B, and illustrates a cartridge which has a big diameter and a great length.

Opening of the cartridge retainer 50 is sensed by the controller 700 whereupon the motor 626 is run for sufficient time to advance the piston rod 627 by a distance that will permit resetting of the locking device 600 when it is closed by the user after cartridge replacement. The detection switch 616 associated with the retainer 50 detects the presence of the cartridge 620 in the retainer 50. In the subsequent step 810 the cartridge retainer 50 is manually moved into the closed position, where it is locked by the locking device 600. In the closed position the detection switch 616 sends a corresponding signal to the controller 700. The insertion condition of the inserted cartridge may furthermore be indicated on the digital display 80. After placing a new cartridge 620 in the retainer 50, the user closes the retainer 50 and the detection switch 616 signals to the controller 700 that a cartridge is present. The latch or locking device 600 may signal to the controller when the retainer 50 is closed. The cartridge exchange process described above is applicable to the other cartridge 622 and its replacement into cartridge retainer 52 according to a routine of steps that corresponds to steps 800 to 810 described above. If that cartridge is also empty, then this will be indicated on the display 80 as in step 800, but indicating Drug A instead of Drug B.

When the device 10 is being brought into use, the controller 700 runs a series of status checks to determine whether the dispense interface is on the device. If not, then the controller will prompt the user to attach the dispense interface. If it is, the controller will ascertain whether a dose of medicament has been dispensed since the dispense interface was attached. Either way, the controller 700 mandates a priming operation as will be described in more detail below.

Initially, the device may be in the state indicated in step 804 of FIG. 12, for example, without either of the Drug A or Drug B cartridges in their respective retainers 50, 52. The user inserts the drug cartridges in the manner described above so that when both are loaded, the display indicates this at step 810 by displaying "Cartridge loaded". Following loading of one or both of the cartridges 620, 622 into the device, the controller 700 may display the prompt "Attach dispense interface" whereupon the user can attach the dispense interface 200 to the cartridge holder 40, whereupon the mandatory prime operation described below may be run.

When the device contains medicament cartridges, the controller 700 senses the attachment (or not) of the dispense interface 200 on the cartridge holder 40, for example by at least one switch or sensor. If the dispense interface is not detected, then the controller 700 prompts for attachment of the dispense interface 200 to the cartridge holder 40. After attachment of the dispense interface, the controller 700 sets the device 10 into a mandatory priming mode. This priming mode serves to expel air that may be present in the dispense interface 200 that has been attached to the cartridge holder 40. If the controller 700 senses the presence of the dispense interface, a mandatory priming operation is required if no dose has been performed by the device since the dispense interface was attached. This provides for the possibility that the user attaches the dispense interface and then takes no further action until a later time. On switching on the device at the later time, a mandatory priming dose will still be required. However, if on device activation the controller 700 senses that a dose has been delivered since the dispense interface was attached, or that the mandatory priming step has already been executed since the dispense interface was attached, then mandatory priming may not be required, in which case the dose function is enabled and the user has the option to either prime or dose.

The controller 700 therefore may include software operative to identify the following states or operational conditions of the device 10:

a. Detecting that the dispense interface 200 has been brought into attachment with the cartridge holder 40;

b. Dispense interface prime state;

c. Drug delivery mode state;

d. Time period Td since last dosing of a medicament greater or less than first preset value Tds; and e. Time period Tp since last priming operation greater or less than second preset value Tps.

Figure 13:
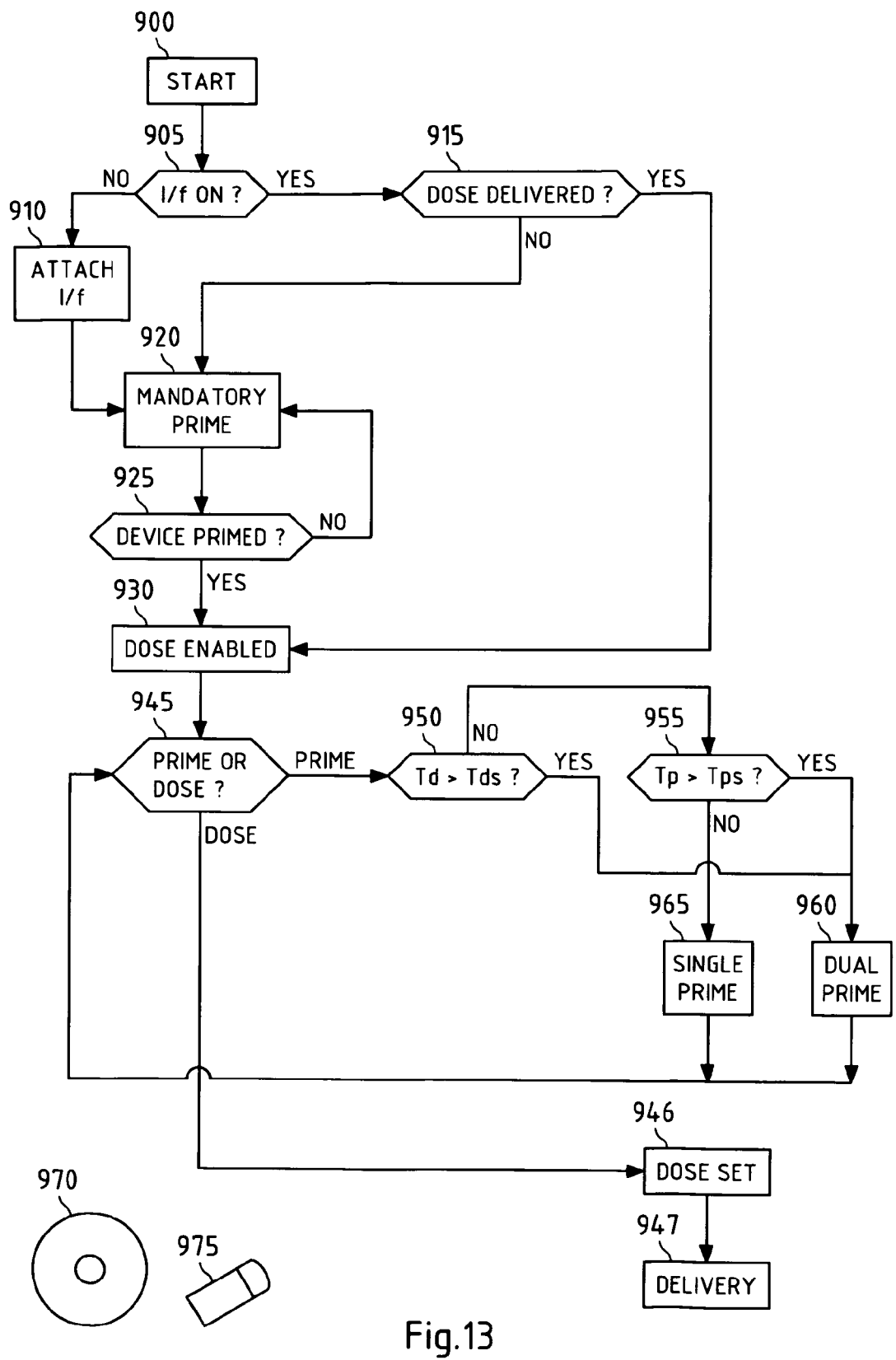
FIG. 13 is a flow chart illustrating operation of a device embodying the present invention.

FIG. 13 is a flow chart with reference to which operational sequences of a device embodying the present invention is described as follows. The device 10 is switched on or started at step 900 whereupon the controller 700 establishes at step 905 whether the dispense interface 200 is attached to the cartridge holder 40 or not. If not, then the controller 700 causes the display 80 to display an appropriate prompt to the user, such as "Attach dispense interface". On attachment of the dispense interface 200, the controller identifies the state of bringing the dispense interface 200 into attachment with the cartridge holder 40 as step 910. If it is determined at step 910 that the dispense interface 200 has been brought into attachment, the controller 700 sets the device 10 into a "Dispense interface prime state", i.e. mandatory prime, at step 920, this forming one of a number of predetermined states of the device. In this state, the drug delivery mode state of the device 10 is disabled by the controller 700 so that a mandatory priming of the device can be executed by the device. This state may be indicated on the display 80 by the software of the controller 700 making the dosing option unavailable. As such, the dose setting buttons 62, 64 are disabled in this state. The display 80 may indicate a priming command or prompt. The software recognises pressing of the 'OK' button 66 and executes a priming operation. The priming operation is controlled by software programmed into the controller 700. Step 925 determines that the mandatory priming operation has been completed. If not, then the prompt for the user to prime the device appears. If the operation has been completed successfully, then the dosing function is enabled at step 930, giving the user the option to dose or prime at the step 945.

If at step 905 the dispense interface is already attached to the device, then the controller needs to decide whether a mandatory priming operation is required or that it is not and the user may have the option to prime. So, if step 905 answers 'yes', then at step 915 the controller 700 determines whether there has been a medicament dose delivered by the device since the dispense interface 200 was attached to the device. If not (i.e. step 915 answers 'no'), then a mandatory priming operation is required and the controller proceeds to step 920 as described above. On the other hand, if the answer at step 915 is 'yes', then the dosing function is enabled at step 930 and the user is given the option to prime or dose at step 945.

In the case of a device having two medicament cartridges, delivery of medicament from the cartridges during performance of the priming operation may be simultaneous or successive. The software controls the drive mechanisms 624, 625 to eject a preset quantity or dose of medicament from the respective cartridges 620, 622. In the case where the cartridges are of different sizes/capacity, the quantity or dose delivered from one cartridge may be different or varied relative to the other. The priming dose is preferably preset to be sufficient for medicament to appear at the distal end of the needle hub 400. Completion of the mandatory priming operation is determined at step 925 whereupon the drug delivery mode state of the device 10 is enabled at step 930.

At step 945, the software within the controller 700 receives a user selection of an optional priming function or dose delivery function. If a dose selection is made at step 945, the controller 700 implements a dose setting routine at step 946 which facilitates the setting of a medicament dose. The set dose is delivered at step 947 on actuation of the injection button 74.

If at step 945 an optional priming operation is selected, the software in the controller 700 selects a preset quantity of medicament to be ejected from the device that is dependent on the operational state identified by the controller 700. In the case of a single medicament reservoir device, the preset quantity of medicament to be ejected during the optional priming mode may be selected by the controller software to differ depending on the identified state of the device. For example, the preset quantity may be one value when a predetermined period of time has elapsed since the previous dose delivered to the patient, or a different value if the controller identifies that a predetermined period of time has elapsed since a previous priming of the device. A further value may be set if it is identified that the medicament cartridge has been replaced.

In the case of a dual cartridge or medicament reservoir device such as the one illustrated in FIGS. 2-11*b*, the varying of the preset quantity during the optional priming mode may be achieved by ejecting medicament from one or both reservoirs depending on which of a number of pre-programmed device states is identified by the controller 700 software. The controller 700 software identifies: a) at step 950 whether a time period Td has elapsed since the last dosing of a medicament from the device that is greater or less than a first preset value Tds; and b) at step 955 whether a time period Tp since the last priming operation is greater or less than a second preset value Tps. In the case where either Td is greater than Tds, or Tp is greater than Tps, then the optional priming is implemented by the controller 700 to dispense a preset quantity of medicament from both cartridges (step 960), thereby effectively 'freshening up' the dispense interface 200.

In the case where the controller 700 software identifies that both Td is less than Tds and Tp is less than Tps, then the controller 700 software actions the optional priming from one of the medicament cartridges only (step 965). The cartridge from which the medicament is ejected during this optional priming is preferably the one of smaller volume in order to preserve the medicament contained therein. The value of either or both of Tds and Tps may be set at, for example, 24 hours, although a different Tds or Tps period could be set at any time between 1 and 24 hours or another period as deemed appropriate for the medical application intended for the device during configuration or set up.

It is noted that the optional priming routine at step 945 may be performed a plurality of times in succession at the discretion of the user. The optional priming operation may therefore be incremental until the user is satisfied or confident that sufficient medicament has been primed, perhaps identified by a few drops at the needle tip, in the device for an injection to be performed.

In the event that there is insufficient medicament remaining in the cartridge(s) to effect a priming function, then the controller will implement the routine illustrated in FIG. 13 to prompt the user to replace the empty cartridge or cartridges. This will cause removal of the dispense interface (see 802 of FIG. 12) which in turn will provoke a mandatory priming function on re-attachment of a dispense interface.

The operational sequences of FIGS. 12 and/or 13 may be performed by a computer program that may be stored on a computer-readable medium such as a CD-ROM 970 or a memory stick 975.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A medicament delivery device for the administration of one or more drug agents, the device having (i) a priming mode for priming the device and (ii) a drug delivery mode for administering delivery of a dose of the one or more drug agents, wherein the device has a plurality of states including a predetermined state, wherein the device comprises a controller operative for:
   determining which of the plurality of states the device is in;
   responsive to the controller determining that the device is in the predetermined state, setting the device in the priming mode and disabling the drug delivery mode during said predetermined state; and
   responsive to the controller determining that the device is in a state different than the predetermined state, setting the device in the drug delivery mode while maintaining enablement of the priming mode through a user interface,
   wherein the user interface is configured to provide a first selectable option for priming the device and a second selectable option for delivering a dose,
   wherein, to set the device in the priming mode and disable the drug delivery mode, the controller is operative to cause the user interface to provide the first selectable option and not the second selectable option to thereby set the device in a mandatory priming mode, and
   wherein, to set the device in the drug delivery mode while maintaining enablement of the priming mode, the controller is operative to cause the user interface to provide both the first selectable option and the second selectable option.

2. A medicament delivery device according to claim 1, wherein the controller determines that the device is in said predetermined state when the controller determines that a dispense interface is placed from a detached to an attached relationship with the device.

3. A medicament delivery device according to claim 1, wherein the controller that the device is in said predetermined state when the controller determines that a dispense interface is attached to the device and no dose of medicament has been dispensed from the device since the attachment of the dispense interface to the device.

4. A medicament delivery device according to claim 1, wherein the medicament delivery device comprises a first retainer and a second retainer each for holding a medicament cartridge containing a drug agent.

5. A medicament delivery device according to claim 4, comprising a detachable dispense interface having a bifurcated conduit for providing fluid communication from the first and second retainers to a unitary outlet.

6. A medicament delivery device according to claim 5, wherein the unitary outlet comprises an attachment for a needle.

7. A medicament delivery device according to claim 4, wherein, to prime the device, the controller is operative to dispense fluid from the medicament cartridges of the first and the second retainers respectively when the device is in said predetermined state.

8. A medicament delivery device according to claim 1, wherein the device comprises an output device and the controller is operative to prompt the user, via the output device, to prime the device when said controller determines the device is in said predetermined state.

9. A medicament delivery device according to claim 4, wherein when the device is set in the drug delivery mode while maintaining enablement of the priming mode, the controller is operative for priming the device from a designated one of the medicament cartridges of the first and the second retainers provided the time that has elapsed since a previous dose or since a previous priming of the device is less than a predetermined value.

10. A medicament delivery device according to claim 4, wherein when the device is set in the drug delivery mode while maintaining enablement of the priming mode, the controller is operative for priming the device from both of the medicament cartridges of the first and the second retainers if the time that has elapsed since a previous dose or since a previous priming of the device is greater than a predetermined value.

11. A medicament delivery device according to claim 4, wherein the controller is operative to eject medicament from the medicament cartridges the first and the second retainers at different rates with respect to one another during enablement of the priming mode.

12. A medicament delivery device according to claim 1, wherein the priming mode ejects a quantity of medicament from the device that is preset by the controller.

13. A medicament delivery device according to claim 12, wherein in the priming mode, the controller is operable to eject the quantity of medicament in a number of discrete units, the number of the discrete units being selected through a user interface.

14. A medicament delivery device according to claim 12, wherein the preset quantity of medicament is dependent on the identified predetermined state.

15. A medicament delivery device according to claim 1, wherein a dose setting device is enabled during the drug delivery mode.

16. A medicament delivery device according to claim 1, wherein the device is hand-held and/or is a pen-type injection device.

17. A medicament delivery device for the administration of a medicament, the device having (i) a priming mode for discharging air or a residual medicament from the device and (ii) a drug delivery mode for administering delivery of a dose of the medicament, wherein the device has a plurality of states including one or more first states and one or more second states, wherein the device comprises:
  a user interface having a priming button for activating the priming mode and a dose-delivery button for activating the drug delivery mode; and
  a controller operative for:
    determining whether the device is in at least one of the one or more first states or at least one of the one or more second states,
    responsive to determining that the device is in at least one of the one or more first states, enabling the priming mode via the priming button and disabling the drug delivery mode via the drug-delivery button during the at least one of the one or more first states, wherein enabling the priming mode and disabling the drug-delivery modes sets the device in a mandatory priming mode, and
    responsive to determining that the device is in at least one of the one or more second states, enabling the priming mode via the priming button and enabling the drug delivery mode via the drug-delivery button during the at least one of the one or more second states.

* * * * *